United States Patent
Solotoff

(10) Patent No.: US 11,918,504 B1
(45) Date of Patent: Mar. 5, 2024

(54) ORTHOTIC DEVICE TO PREVENT HYPEREXTENSION

(71) Applicant: PREFERRED PRESCRIPTION, INC., Hollywood, FL (US)

(72) Inventor: Brandon Solotoff, Boca Raton, FL (US)

(73) Assignee: Preferred Prescription, INC., Hollywood, FL (US)

( * ) Notice: Subject to any disclaimer, the term of this patent is extended or adjusted under 35 U.S.C. 154(b) by 32 days.

(21) Appl. No.: 17/209,395

(22) Filed: Mar. 23, 2021

Related U.S. Application Data

(63) Continuation-in-part of application No. 17/020,072, filed on Sep. 14, 2020.

(Continued)

(51) Int. Cl.
*A61F 5/37* (2006.01)

(52) U.S. Cl.
CPC ............ *A61F 5/3715* (2013.01); *A61F 5/373* (2013.01)

(58) Field of Classification Search
CPC .. A61F 5/00; A61F 5/37; A61F 5/3715; A61F 5/3723; A61F 5/373; A61F 5/01;
(Continued)

(56) References Cited

U.S. PATENT DOCUMENTS

| | | | |
|---|---|---|---|
| 1,510,408 A * | 9/1924 | Lychou | A61F 5/0106 602/26 |
| 2,519,226 A | 8/1950 | Coe | |

(Continued)

FOREIGN PATENT DOCUMENTS

| | | |
|---|---|---|
| DE | 102008024748 A1 | 12/2009 |
| FR | 2440187 A1 | 5/1980 |
| GB | 2260495 | 4/1993 |

OTHER PUBLICATIONS

Baldwin, James, Anatomic dimensions of the patella measured during total knee arthroplasty, Feb. 20, 2005 [online], [Retrieved on Aug. 18, 2022], Retrieved from Internet: https://pubmed.ncbi.nlm.nih.gov/15902866/#:~:text=The%20articular%20surface%20of%20the,and%20displaced%20medially%203.6%20mm. (Year: 2005).*

(Continued)

*Primary Examiner* — Ophelia A Hawthorne
*Assistant Examiner* — Gina McCarthy
(74) *Attorney, Agent, or Firm* — Thomas A. O'Rourke; James Bongiorno; O'Rourke IP Law PLLC

(57) ABSTRACT

An orthotic device restrains a portion of the movement of a wearer's limb about a joint to train the wearer's muscles to be so limited after the device is no longer worn, preventing hyperextension. The device includes: a first and second tubular portions, and at least one resistance band. The first and second tubular portions encircle respective portions of the limb on opposite sides of a joint, and apply compression. The tubular portions are formed of elastic material, and are joined together to orient an axis of the second tubular portion at an angle to an axis of the first tubular portion, when undeformed. The first and second ends of the resistance member(s) are fixedly secured to selective positions on the first and second tubular portions, respectively, and has a length configured to bias only a portion of the range of movement of the limb away from full extension.

16 Claims, 3 Drawing Sheets

Related U.S. Application Data

(60) Provisional application No. 63/002,461, filed on Mar. 31, 2020, provisional application No. 62/934,587, filed on Nov. 13, 2019.

(58) Field of Classification Search
CPC .... A61F 5/0102; A61F 5/0104; A61F 5/0106; A61F 5/0109; A61F 5/0111; A61F 5/0118; A61F 5/0123; A61F 5/0125; A61F 5/013; A61F 5/04; A61F 5/042; A61F 2005/0134; A61F 2005/0169; A61F 2005/0179; A61F 5/012; A61F 5/0127; A61F 5/028; A61F 13/061; A61H 1/02; A61H 1/0237; A61H 1/024; A41D 31/18
See application file for complete search history.

(56) References Cited

U.S. PATENT DOCUMENTS

| | | | |
|---|---|---|---|
| 2,743,792 A | 5/1956 | Ransom | |
| 2,777,439 A | 1/1957 | Tuttle | |
| 2,832,334 A | 4/1958 | Whitelaw | |
| 3,320,822 A | 5/1967 | Tatom | |
| 3,323,518 A | 6/1967 | Swanson | |
| 3,651,903 A | 3/1972 | Butler | |
| 3,683,897 A | 8/1972 | Shield | |
| 3,785,371 A | 6/1974 | Lewis | |
| 3,927,665 A * | 12/1975 | Wax | A61F 5/028 602/19 |
| 3,929,335 A | 12/1975 | Malick | |
| 3,976,057 A | 8/1976 | Barclay | |
| 4,214,577 A | 7/1980 | Hoy | |
| 4,487,199 A | 12/1984 | Saringer | |
| 4,492,227 A * | 1/1985 | Senn | A61F 13/061 602/26 |
| 4,651,719 A | 3/1987 | Funk | |
| 4,776,437 A | 10/1988 | Ishibashi | |
| 4,801,138 A | 1/1989 | Airy | |
| 4,887,590 A * | 12/1989 | Logue | A61F 5/0125 602/26 |
| 5,087,868 A | 2/1992 | Ishibashi | |
| 5,103,811 A | 4/1992 | Crupi | |
| 5,346,452 A | 9/1994 | Ku | |
| 5,352,190 A | 10/1994 | Fischer | |
| 5,472,412 A | 12/1995 | Knoth | |
| 5,651,536 A | 7/1997 | Daul | |
| 5,730,710 A * | 3/1998 | Eichhorn | A61F 5/012 602/26 |
| 5,735,807 A * | 4/1998 | Cropper | A61F 5/0109 602/26 |
| 5,978,966 A * | 11/1999 | Dicker | A41D 31/18 2/69 |
| 6,080,123 A | 6/2000 | Pansiera | |
| 6,117,097 A * | 9/2000 | Ruiz | A61F 5/0109 602/26 |
| 9,333,107 B2 | 5/2016 | Potter | |
| 9,844,454 B2 | 12/2017 | Garrish | |
| 2011/0054870 A1 | 3/2011 | Dariush | |
| 2013/0252216 A1 | 9/2013 | Clavin | |
| 2014/0147821 A1 | 5/2014 | Bernard-Paroly | |
| 2014/0272891 A1 | 9/2014 | Saladino | |
| 2014/0358053 A1 | 12/2014 | Triolo | |
| 2015/0132731 A1 | 5/2015 | Khan | |
| 2015/0187226 A1 | 7/2015 | Slovenski | |
| 2016/0023046 A1 | 1/2016 | Evin | |
| 2016/0367391 A1 * | 12/2016 | Paulos | A61F 5/0106 |
| 2017/0087000 A1 * | 3/2017 | Cain | A61F 5/0127 |

OTHER PUBLICATIONS

Press Fit Forces Stress Design Calculator, Jun. 18, 2018, available at: www.engineersedge.com/calculators/machine-design/press-fit/press-fit.htm.

"Three General Types of Fit," available at www.mmto.org/dclark/Reports/Encoder%20Upgrade/fittolerences%20%5BRead-Only%5D.pdf., Jul. 8, 2019.

"Engineering Fit," available at: https://en.wikipedia.org/wiki/Engineering_fit, Jul. 8, 2019.

Noyes' Knee Disorders: Surgery, Rehabilitation, Clinical Outcomes, Ch. 29, "Correction of Hyperextension Gait Abnormalities: Preoperative and Postoperative Techniques,".
Timothy P. Heckmann, Frank R. Noyes, Sue D. Barber-Westin, 2nd Ed., Elsevier, 2016.

* cited by examiner

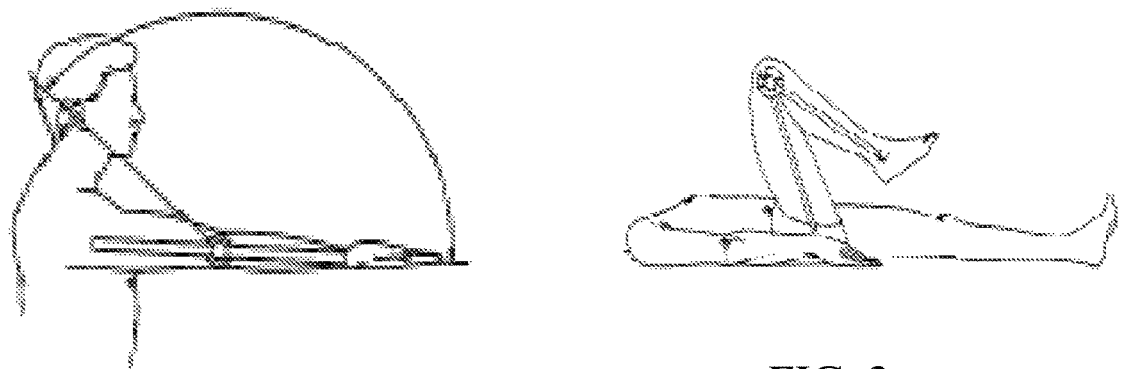
FIG. 4
FIG. 3
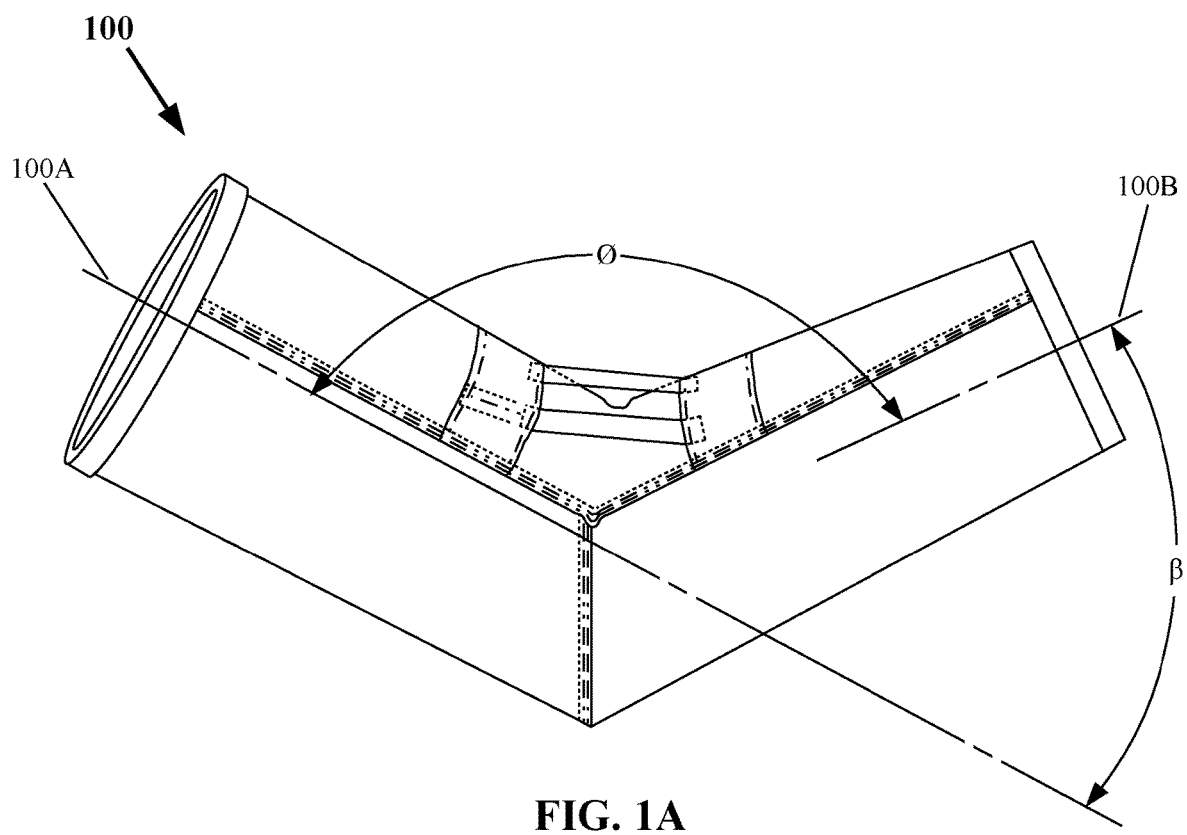
FIG. 1A

ORTHOTIC DEVICE TO PREVENT HYPEREXTENSION

CROSS REFERENCES TO RELATED APPLICATIONS

This application claims priority on U.S. Provisional Application Ser. No. 63/002,461, filed on Mar. 31, 2020, having the title "Compression Sleeve with Resistance Bands," and is a continuation in part of U.S. patent application Ser. No. 17/020,072, filed on Sep. 14, 2020, which claims priority on U.S. Provisional Application Ser. No. 62/934,587, filed on Nov. 13, 2019, having the title "Compression Garments," all disclosures of which are incorporated herein by reference.

FIELD OF THE INVENTION

This disclosure relates generally to orthotic devices, and more particularly to an orthotic device that is configured to train the motion of a wearer's limb to prevent hyperextension of a joint (knee/elbow/ankle) when moving around and being active once the device is no longer being worn.

BACKGROUND OF THE INVENTION

The joints of the human body, including the knee, elbow, and ankle, are susceptible to various different injuries, one of which is hyperextension. Hyperextension of the knee may occur by pushing the femur or patella over the tibia and placing excess stress upon one or more of the major ligaments within the knee joint. Hyperextension of the knee can cause damage to the associated ligaments and cartilage, and also to other stabilizing structure of that joint. Hyperextension of the knee may occur as a result of a sudden impact to the front of the knee, which may occur while participating in athletic events. However, hyperextension of the knee may also develop as a result of an abnormal gait. In particular, "patients with chronic insufficiency of the lateral and posterolateral structures of the knee may develop a gait abnormality that is characterized by excessive knee hyperextension during the stance phase (initial contact or heel strike, loading response, midstance, and toe-off) of the gait cycle . . ." Noyes' Knee Disorders: Surgery, Rehabilitation, Clinical Outcomes, Timothy P. Heckmann, Frank R. Noyes, and Sue D. Barber-Westin, chap. 29, p. 4, Correction of Hyperextension Gait Abnormalities: Preoperative and Postoperative Techniques, 2nd Edition, Elsevier, Philadelphia, PA, 2016.

Similarly, a person's elbow joint may become hyperextended if the humeroulnar joint is bent backwards beyond it natural range of motion, which would most often occur while playing contact sports, but may also occur as a result of vigorous physical activity. The ankle joint is also susceptible to hyperextension.

The herein disclosed orthotic device is particularly configured to address joint issues with respect to hyperextension and/or osteoarthritis, by being particularly configured to train a wearer to restrain a portion of the motion of the joint, so that once the brace is no longer being worn, the person will normally tend to naturally limit such movement at that joint while being active.

It is noted that citing herein of any patents, published patent applications, and non-patent literature is not an admission as to any of those references constituting prior art with respect to the herein disclosed and/or claimed apparatus.

OBJECTS OF THE INVENTION

It is an object of the invention to provide an orthotic device that provides support to a knee joint, and/or an elbow joint, and/or an ankle joint.

It is another object of the invention to provide an orthotic device that is configured to treat and/or prevent hyperextension of a human joint.

It is a further object of the invention to provide an orthotic device that is configured to restrain a portion of the movement of a human joint to train the wearer's muscles and movement to be so limited even after the device is no longer being worn.

It is another object of the invention to provide an orthotic device that is configured to treat arthritic joint locking.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

An orthotic device, in accordance with at least one embodiment disclosed herein, may be configured to restrain a portion of the movement of a wearer's limb about a joint to train the wearer's muscles and movement to be so limited after the orthotic device is no longer being worn, to prevent hyperextension. The orthotic device may be formed to include: a first tubular portion, a second tubular portion, and at least one resistance band. The first tubular portion is configured to encircle a portion of a limb of the wearer on a first side of a joint, and apply a first level of compression; and the second tubular portion is configured to encircle a portion of the limb of the wearer on a second side of the joint, and apply a second level of compression The first tubular portion and the second tubular portion may each be fondled of an elastic material, and may be joined together to orient an axis of the second tubular portion at an angle to an axis of the first tubular portion, when undeformed. The at least one resistance member may have a first end fixedly secured to a selective position on the first tubular portion, and a second end fixedly secured to a selective position on the second tubular portion. The length of each of the at least one resistance members and a positioning of the first and second ends thereof are configured to bias only a portion of the range of movement of the limb away from full extension.

The selective positioning for the securement of the first end of each of the at least one resistance members is at least one inch away from the joint; and the selective positioning for the securement of the second end of each of the at least one resistance members is also at least one inch away from the joint.

To better ensure the sufficiency of the attachment of the ends of each of the at least one resistance members to the respective tubular sections, those ends may be overlaid by first and second cross-wise straps. Moreover, those secured ends of each of the at least one resistance members may extend across an entire width of the corresponding cross-wise strap.

The at least one resistance member may be configured to begin biasing a leg away from full extension upon reaching an angle of 24 to 34 degrees, and may also reach ultimate elongation prior to the leg reaching its fully extended position. In another embodiment, the at least one resistance member may be configured to bias a leg away from full extension upon reaching an angle of 14 to 24 degrees, and may reach ultimate elongation prior to the leg reaching its fully extended position. In yet another embodiment, the at least one resistance member may be configured to bias a leg away from full extension upon reaching an angle of between 4 to 14 degrees, and may reach ultimate elongation prior to the leg of reaching its fully extended position.

The first and second cross-wise straps may each be formed with a length for a first end thereof to extend beyond a lateral side of the at least one resistance member a distance being one to three times a width of the at least one resistance member, and for a second end thereof to extend beyond a medial side of the at least one resistance member a distance being one to three times the width of the at least one resistance member. Also, each of the first and second cross-wise straps may be formed with a width being between one to three times a width of the at least one resistance member.

In one embodiment, the at least one resistance member may be a first resistance member and a second resistance member, where a width of each of the first resistance member and the second resistance member may be about 10 percent to 20 percent of a lateral extent of either the first tubular portion and the second tubular portion in one embodiment; or may be about 20 percent to 35 percent of a lateral extent of either the first tubular portion and the second tubular portion in another embodiment; or may be about 35 percent to 45 percent of a lateral extent of either the first tubular portion and the second tubular portion.

Each resistance member may be fixedly secured using stitching, and may be formed of a two-way stretch fabric. The elastic material of the first and second tubular portions may be a four-way stretch fabric. Lastly, each of the first and second cross-wise straps may be formed of a non-stretch material.

BRIEF DESCRIPTION OF THE DRAWINGS

The description of the various example embodiments is explained in conjunction with appended drawings, in which:

FIG. 1A is the side perspective view of FIG. 1, but highlighting the angle between the tubular sections;

FIG. 3 is a view illustrating range of motion for the knee;

FIG. 4 is a view illustrating range of motion for the elbow; and

DETAILED DESCRIPTION OF THE INVENTION

Figure 2:
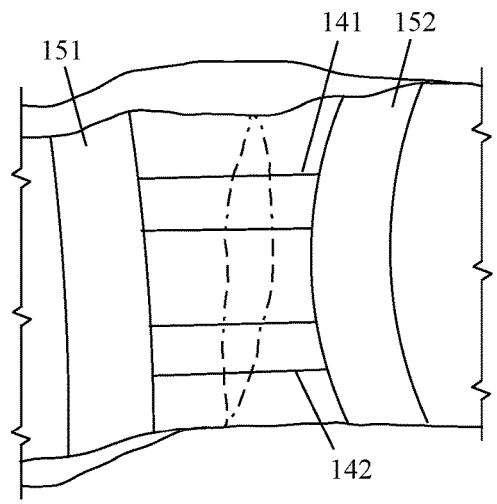
FIG. 2 is a top perspective view of the orthotic device shown in FIG. 1.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed and/or claimed apparatus/method.

Furthermore, any reference made throughout this specification to "one embodiment" or "an embodiment" means that a particular feature, structure or characteristic described in connection therewith is included in at least that one particular embodiment. Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

The terms "flexible" and "resilient" are used herein to distinguish characteristics of portions of certain features of the disclosed orthotic device. Use of the term "flexible" indicates that the described element is capable of repeated bending such that it may be bent into different shapes and does not retain a general shape, but instead readily deforms when force is applied. Use of the term "resilient" indicates that the described element has such flexible features and also has a tendency to return to its initial general shape without permanent deformation once a force that causes such flexure is removed. Use of the term "semi-rigid" indicates that the described element may have some degree of flexibility or resiliency.

This disclosure describes and illustrates an orthotic device that is configured to restrain only a portion of the movement about a joint (knee, elbow, and/or ankle) to train the wearer's muscles and movement to be so limited even after the device is no longer being worn, to prevent hyperextension. Although the device disclosed herein may be adapted for use on any portion of a limb to treat the joint—e.g., the knee joint, the elbow joint, and/or the ankle joint, the following description may be generally made with reference to it being particularly adapted for use on one of those joints (e.g., the knee), with the understanding that it may also be similarly adapted for use with respect to any of those other joints as well.

The main (tubular) portions of the orthotic device may be formed of one or more pieces of elastic material in various different embodiments.

For example, in one embodiment the orthotic device may be formed of a first, generally tubular cuff and a second, generally tubular cuff, where the first cuff is received onto and encircles one portion of the limb (e.g., the forearm) and the second cuff is received on and encircles another portion of the limb (e.g., the upper arm). In this embodiment, the joint itself may not be surrounded or overlaid by the elastic material of either cuff.

Figure 1:
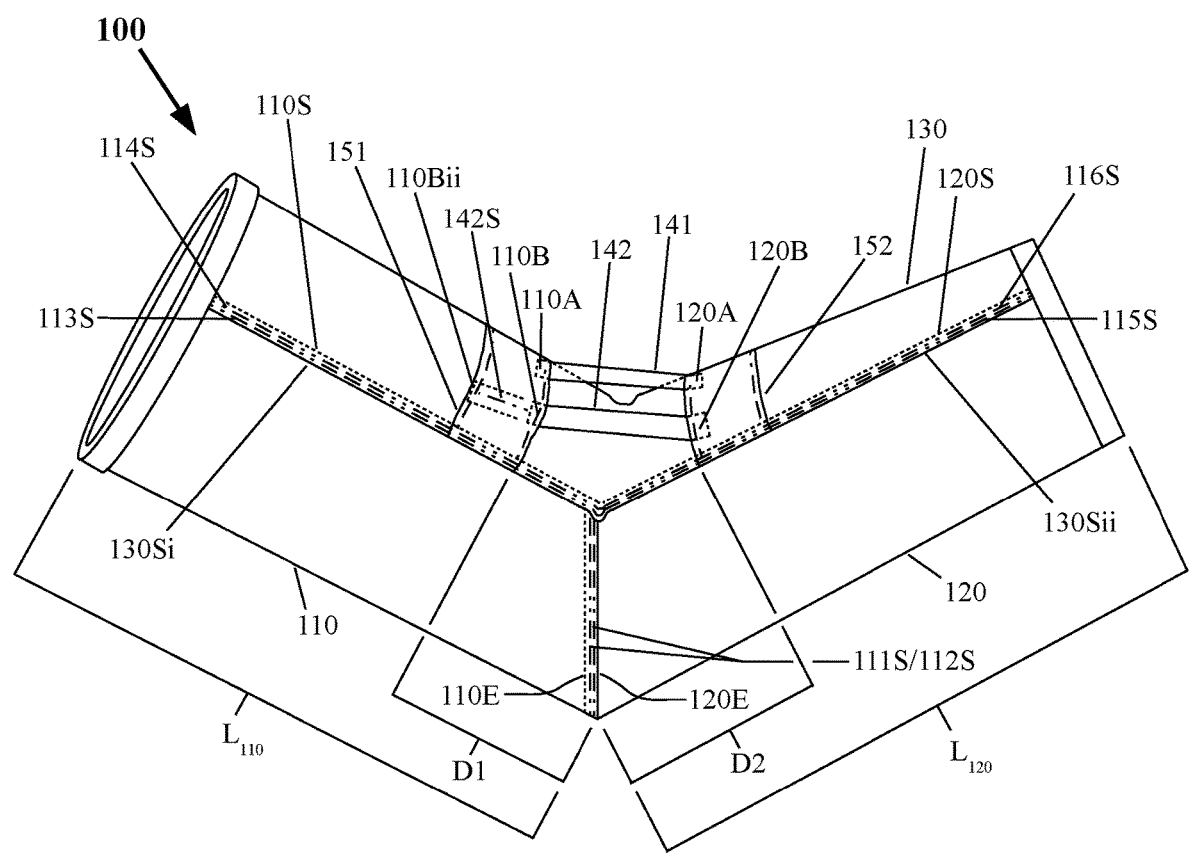
FIG. 1 is a side perspective view of a first embodiment of an orthotic device formed of at least one sleeve with resistance bands secured thereto and configured to restrain a portion of the movement of a joint to train the wearer's muscles and corresponding movements to be so limited even after the sleeve is no longer being worn.

FIG. 1 and FIG. 2 illustrate another embodiment—an orthotic device 100. The orthotic device 100 may be fondled of multiple sleeve portions, e.g., a first sleeve portion 110, a second sleeve portion 120, and a third sleeve portion 130. The first sleeve portion 110 and second sleeve portion 120 may be formed/positioned to respectively apply pressure primarily against the back and a portion of the sides of the upper arm and lower arm, while the third sleeve portion 130 may be formed/positioned to apply pressure primarily against the front and a portion of the sides of the upper arm and lower arm. The third sleeve portion may also be formed of two separate tubular portions that are fixedly secured to each other to prevent bunching of the material when the joint is flexed. Altogether, the first sleeve portion 110, the second sleeve portion 120, and third sleeve portion 130 form first and second generally "tubular" sections (e.g., cylindrical sections, and/or conical frustum sections that may have a large axial length to radius ratio, being at least greater than one), which tubular sections may encircle a portion of the limb that may include a portion of the joint itself.

To account for the size difference in the limbs of various different wearers, the sleeve portions of the orthotic device 100 may be custom formed for each user based on measurement of the wearer's forearm/upper-arm/elbow dimensions (or the leg/knee/foot dimensions). Alternatively, the sleeve portions of the orthotic device 100 may be formed in an extensive range of different sizes, including, but not limited to, an extra-small size, a small size, a medium size, a large size, an extra-large size, a double extra-large size, a triple extra-large size, etc.

The end 110E of the first sleeve portion 110 and the end 120E of the second sleeve portion 120 may be joined together by a seam, which may be any suitable type of seam known in the art, including, but not limited to, a lap seam, with a single or double row of stitching (e.g., stitching 111S and/or stitching 112S). The length of the near side 110S of the first sleeve portion 110 may be joined to the comparable length of the near side 130Si of the third sleeve portion 130 by a seam using stitching (e.g., stitching 113S/114S), and the near side 120S of the second sleeve portion 120 may also be joined to the near side 130Sii of the third sleeve portion 130 by a seam using stitching (e.g., stitching 115S/116S). The far side of the first sleeve portion 110 may be joined to the far side of the third sleeve portion 130 in a similar manner (not shown), and the far side of the second sleeve portion 120 may also be joined to the far side of the third sleeve portion 130 in a similar manner (not shown).

The first and second generally tubular sections formed by the joined sleeve portions (e.g., sleeve portions 110, 120, and 130) may have corresponding axes, i.e., 100A and 100B, that may be oriented at an angle θ to each other when undeformed, as shown in FIG. 1A. The tubular shape formed by the first sleeve portion 110 and corresponding portion of the third sleeve portion 130 may be formed to be received primarily upon one portion of the limb of the wearer (e.g., encircling part of the leg and extending from the knee joint up to the thigh), while the tubular shape of the second sleeve portion 120 and corresponding portion of the third sleeve portion 130 may be formed to be received upon another portion of the limb of the wearer (i.e., to encircle the leg of the wearer extending from the knee joint to the calf).

The first sleeve portion 110, the second sleeve portion 120, and the third sleeve portion 130 may each be formed of one or more layers of an elastic material that may include, but is not limited to: a spandex, a stretch vinyl, polyester, bamboo, any blends of those materials, and any other suitable fabrics known in the art of orthotic braces and sleeves. Each of the sleeve portions (e.g., the first sleeve portion 110, the second sleeve portion 120, and the third sleeve portion 13) are also each preferably formed of a four-way stretch fabric. Therefore, the tubular portions formed by the first sleeve portion 110, the second sleeve portion 120, and the third sleeve portion 130 may in combination be formed to apply a level of compression to those encircled portions of the wearer's body. In one embodiment the elastic of those sleeve portions may exhibit a compression pressure in the range of 2 mm Hg to 5 mm Hg, and in another embodiment the elastic material may exhibit a compression pressure in the range of 5 mm Hg to 8 mm Hg, and in yet another embodiment the elastic material may exhibit a compression pressure in the range of 8 mm Hg to 15 mm Hg, and in another embodiment the elastic material may exhibit a compression pressure in the range of 15 mm Hg to 30 mm Hg, and in other embodiments other ranges or a combinations of those ranges may instead be used. The level of compression respectively applied by the tubular portions formed by the first sleeve portion 110, the second sleeve portion 120, and the third sleeve portion 130 may help to maintain the sleeve 100 at the proper position on the wearer's leg during flexion and extension.

To restrain a portion of the relative motion of the limb, e.g., the lower leg with respect to the upper leg, to freely approach but not reach full extension (i.e., limiting extension to about 90-percent, where 100 percent equates to full extension), in order to train the muscles (i.e., develop muscle memory) to avoid expansive motion that would tend to lead to a hyperextended condition when the orthotic device 100 is not being worn, a wide resistance member may have one of its ends be secured (e.g., by stitching) at a selective position 110A on the first sleeve portion 110, with its other end secured at a selective position 110B on the second sleeve portion 120.

In one embodiment, the wide resistance member may have its width be a substantial portion of the lateral extent of the limb where it is attached (e.g., sixty percent to eighty percent of the width of the limb). In another embodiment, instead of using one wide resistance member, two (or more) narrow width resistance members may be used, being, for example, the resistance member 141 and resistance member 142 shown in FIG. 1. The resistance member 141 may have one of its ends secured at a selective position 110A on the first sleeve portion 110, and its other end secured at a selective position 120A on the second sleeve portion 120. The resistance member 142 may have one of its ends secured at a selective position 110B on the first sleeve portion 110, and its other end secured at a selective position 120B on the second sleeve portion 120. Each of the resistance members 141/142 may have a width (see FIG. 2) that may be a portion of the extent/diameter of the sleeve portions at the joint (i.e., proximate to stitching 111S/112S), being a width of about 10 percent to 20 percent of the diameter of the sleeve in one embodiment, or about 20 percent to about 35 percent of the sleeve diameter in another embodiment, or about 35 percent to 45 percent in yet another embodiment, or a combination of such width ranges or other width range may be used in other embodiments.

The length of the resilient resistance members 141 and 142 may be set so that when the first and second tubular portions of the sleeve 100 are undeformed (i.e., the respective axes 110A and 100B are at the angle θ, as seen in FIG. 1A), the resilient resistance members 141 and 142 are also undeformed. Thus, each of the parameters that contribute to forming the sleeve 100 (i.e., the lengths of the resistance members, the shape and joining of the sleeve portions, etc.) may all be calibrated to provide the angle θ at which there is no deformation, to specifically provide biasing against full extension of the limb with respect to the joint for only a small angular (range of motion) portion of the final joint movement of the limb before full extension occurs.

For example, although the typical leg when straightened (e.g., when positioned on the ground) may be at 0 degrees, some overextension is common while standing or moving around, so the normal full range of motion is minus 6 degrees to 140 degrees in men, and minus 5 degrees to 143 degrees in women (see FIG. 3). Therefore, the sleeve 100 may be formed such that deformation of the resilient members occurs when the angle β (see FIG. 1A), which is the complement of the angle θ and which angle β reflects the described range of motion angles, may be in the range of about 24-34 degrees in one embodiment, or may be in the range of about 14-24 degrees in another embodiment, or may be in the range of about 4-14 degrees in yet another embodiment, or a combination of such ranges or other ranges of angles may be used in other embodiments. It is preferable that the resilient members only bias the limb just prior to full extension (e.g., for at least ten degrees of the range of motion), so as to not interfere with the majority of the range of motion of the limb (e.g., the range of motion between 25 degrees and 140 degrees will not be affected by the resilient resistance members 141 and 142). Separate braces may be made for men and form women, and separate braces may be made for each wearer that specifically limits the range of motion as prescribed for the physiology of the individual wearer.

The sleeve may be similarly formed for an arm, which typically has a range of motion of between 0 degrees and 150 degrees (see FIG. 4).

In another embodiment, a series of braces may be tailored specifically to be worn by men, while another series of braces may be specifically tailored to be worn by women. In yet another embodiment, the sleeve 100 may be tailor made for each wearer, and may be manufactured to specifically limit the range of motion as prescribed for the physiology of the individual wearer by a doctor.

The resistance members 141/142 may be formed of any suitable resilient material, including, but not limited to, a thermoplastic elastomer, a polyurethane, etc., and may be a four-way stretch fabric, or more preferably may be a two-way stretch fabric, being able to stretch slightly in the axial direction. In another embodiment the resistance members 141/142 could be formed of a material that is not resilient, which would affect the length of those members that would need to be used, to limit motion with respect to the joint as the limb approaches full extension; however, some degree of resilience is preferred for resistance members 141 and 142. Moreover, it is desirable in one embodiment that the stretch fabric used for the resistance members 141 and 142 may reach its ultimate elongation prior to the limb of the wearer reaching its fully extended position. In addition, the modulus of the stretch fabric used for the resistance members 141 and 142 may be chosen for the particular wearer and the specific use. For example, the wearer's legs are generally stronger that the arms of the same wearer, and therefore a higher modulus would normally be used for the sleeve 100 that is configured for use on the person's leg, than a sleeve 100 that is configured for use on the person's a"u.

The selective positioning for attachment of the ends of the resilient member or members in one embodiment may preferably be just slightly beyond the anatomical joint itself, as shown in FIG. 1, which may permit use of a short length of the elastic material, and may serve to provide the wearer with less leverage to elongate the resilient member than if the end/ends were attached closer to the distal ends of the orthotic device 100.

Merely to be exemplary, where the orthotic device 100 is formed in a small size and for the wearer's arm, the distance D1 to the attachment of the resilient members 141/142 at points 110A/110B may be about 1.0 inches to 1.5 inches in one embodiment, and may be 1.5 inches to 2.0 inches in another embodiment, and may be 2.0 inches to 3.0 inches in yet another embodiment, and a combination of such distance ranges or other distance ranges may alternatively be used. The distance D2 to the attachment of the resilient members 141/142 at points 120A/120B may be according to the ranges used for the distance D1. Although the distance D1 need not be the same as distance D2, in one embodiment they may be made to be the same distance.

The length $L_{110}$ and length $L_{120}$ may be varied for each wearer so that the tubular portions may respectively extend to reach the wrist and the shoulder of that person when used on the arm, although shorter lengths may alternatively be used so as to not extend so far, because the greater lengths may require more strength to pull the longer tubular portions onto the full extent of the limb; however the length $L_{110}$ and length $L_{120}$ are each preferably at least five or six inches long. Other length dimensions may be used in other embodiments.

To better distribute the loads from each of the resilient members 141/142 to the two tubular portions, the respective joining at each of 110A and 110B may be overlaid by a cross-wise oriented strap member 151, and the respective joining at each of 120A and 120B may be overlaid by a cross-wise oriented strap member 152 (see FIG. 2—being cross-wise with respect to the axes 100A and 100B). Each of the strap members 151 and 152 may be fixedly secured to the respective tubular portions using any one or more suitable methods of joining, including, but not limited to, adhesive, stitching, etc. To assure a good connection between the strap member 151 and the resilient members 141/142 at the respective joining at 110A and 110B, and also between the strap member 152 and the resilient members 141/142 at the respective joining at 120A and 120B, concentrated stitching may be used at those joining locations. The cross-wise oriented strap members 151 and 152 may each have a length sufficient to span beyond the lateral-most securement (stitching) of the resilient members 141/142 to the tubular portions, as seen in FIG. 2, and may preferably extend beyond the resilient members a distance that is at last one to three times the width of the resilient member. Also, for the exemplary orthotic device 100 with dimensions described in the last two paragraphs, the cross-wise oriented strap members 151 and 152 may each have a width being between one to three times the width of the resilient members 141/142.

In addition, in another embodiment, each of the resilient members 141/142 may extend beyond the respective joining at 110A/110B and at 120A/120B, as seen for example for the resilient member 142 in FIG. 1, so that each may extend to terminate proximate to, or even coterminous with, the distal side of the strap (e.g., resilient member 142 may extend to 110Bii), and each may be stitched (e.g., using stitching 142S) to both the respective strap member (e.g., to strap member 151) and to third sleeve portion 130 along that entire extended length. (Note, in yet another embodiment, the resilient members 141 and 142 and the strap members 151 and 152 may be integrally formed as a single unitary member, which may be substantially inelastic).

The strap members 151 and 152 may be formed of the same material as either the sleeve portions 110/120 or the resilient members 141/142. In another embodiment, the strap members 151 and 152 may be formed of a flexible material that may be much less resilient than either the sleeve portions 110/120 and the resilient members 141/142, or may not exhibit much elastic stretching at all, and which material may include, but is not limited to, a nylon or a polyester.

The angle θ between the first sleeve portion 110 and the second sleeve portion 120 may be between 90 degree to 170 degrees, with the resilient members 141/142 each being fully elongated (i.e., being without folds) but not yet stretched to be deformed at all. The angle θ between the first sleeve portion 110 and the second sleeve portion 120 may more preferably be between 120 degree to 170 degrees, and is most preferably (i.e., is formed in another embodiment) to be between 140 degree to 170 degrees.

When the orthotic device 100 is worn by a person, as he or she extends a portion of the limb about the joint (e.g., extends the lower leg about the knee relative to the upper leg), and as the angle approaches full extension (e.g., exceeds 170 degrees for the upper leg and lower leg with respect to the knee joint), the resilient members 141/142 will start to be stretched, providing a substantial resistance force to inhibit further extension. In one embodiment, the resilient members 141/142 may be configured to reach full elongation as the leg extension reaches 180 degrees.

After 2-3 days of more of using the orthotic device, the wearer will develop muscle memory and will naturally tend to stop extending the limb out to full extension, which will serve to prevent hyperextending of the joint by the person even while no longer wearing the sleeve.

Figure 5:
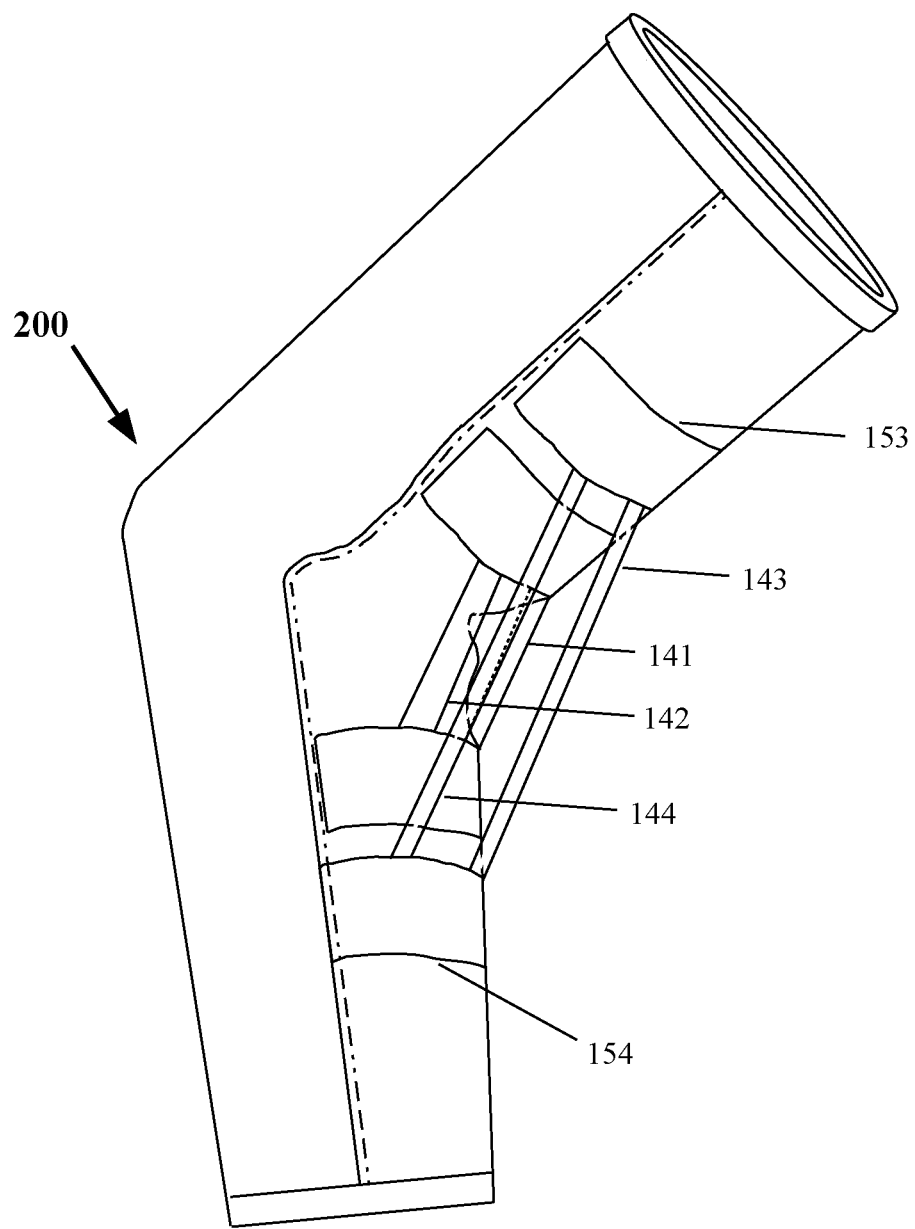
FIG. 5 is a side perspective view of a second embodiment of an orthotic device with at least one sleeve with resistance bands configured to restrain a portion of the movement of a joint to train the wearer's muscles and corresponding movements to be so limited even after the sleeve is no longer being worn.

A second embodiment—orthotic device 200—is shown in FIG. 5. The orthotic device 200 may be formed the same as orthotic device 100, and may additionally include resilient members 143/144 which may be joined to the sleeve portions beyond the attachment of the resilient members 141/142, as shown in FIG. 5, and may have its attachment be similarly reinforced using strap members 153 and 154. The ends of the inner set of resilient members 141/142 may be positioned a first distance away from the knee joint, while the ends of the outer set of resilient bands 143/144 may be positioned a second distance away from the knee joint. The additional resistance bands may be used for added resistance particularly for the larger size knee brace for a larger more muscular wearer that may need greater resistance applied in order to form the required muscle memory.

While illustrative implementations of one or more embodiments of the disclosed sleeve are provided hereinabove, those skilled in the art and having the benefit of the present disclosure will appreciate that further embodiments may be implemented with various changes within the scope of the disclosed sleeve. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. An orthotic device configured to bias only a portion of the movement of a wearer's limb about a joint to train the wearer's muscles and movement to be limited after said orthotic device is no longer being worn to prevent hyperextension, said orthotic device comprising:
    a first tubular portion, said first tubular portion comprising an elastic material;
    a second tubular portion, said second tubular portion comprising an elastic material;
    wherein said second tubular portion is joined to said first tubular portion to orient an axis of said second tubular portion at an angle to an axis of said first tubular portion, when undeformed;
    wherein said first tubular portion is configured to encircle a portion of a limb of the wearer on a first side of a joint, and apply a first level of compression;
    wherein said second tubular portion is configured to encircle a portion of the limb of the wearer on a second side of the joint, and apply a second level of compression;
    at least one resistance member, each said at least one resistance member having a first end fixedly secured to a selective position on said first tubular portion, and a second end fixedly secured to a selective position on said second tubular portion;
    wherein a length of each said at least one resistance member and a positioning of said first and second ends are configured to bias only up to fourteen degrees of the range of movement of the limb being just prior to full extension, to train the wearer's muscles and movement to be limited after said orthotic device is no longer being worn to prevent hyperextension;
    a first cross-wise strap;
    a second cross-wise strap;
    wherein said first cross-wise strap has an elongated shape with a length oriented transverse with respect to an axial direction of said first tubular portion; wherein an entirety of said length of said first cross-wise strap is stitched to said first tubular portion, with a portion of said first cross-wise strap overlaying and being stitched to said first end of said resistance member to distribute loads from said first end of said resistance member to said first tubular portion; and wherein said length of said first cross-wise strap extends around only a portion of said first tubular portion; and
    wherein said second cross-wise strap has an elongated shape with a length oriented transverse with respect to an axial direction of said second tubular portion; wherein an entirety of said length of said second cross-wise strap is stitched to said second tubular portion, with a portion of said second cross-wise strap overlaying and being stitched to said second end of said resistance member to distribute loads from said second end of said resistance member to said second tubular portion; and wherein said length of said second cross-wise strap extends around only a portion of said second tubular portion.

2. The orthotic device according to claim 1, wherein said selective position for said fixedly secured first end of each said at least one resistance member is in a first range of one inch to three inches away from the joint; and
wherein said selective position for said fixedly secured second end of each said at least one resistance member is in a second range of one inch to three inches away from the joint.

3. The orthotic device according to claim 2, wherein said fixedly secured first end of each said at least one resistance member to said first tubular portion extends across a width of said first cross-wise strap; and
wherein said fixedly secured second end of each said at least one resistance member to said second tubular portion extends across a width of said second cross-wise strap.

4. The orthotic device according to claim 3, wherein said first cross-wise strap comprises a length for a first end of said first cross-wise strap to extend beyond a lateral side of said at least one resistance member a distance being one to three times a width of said at least one resistance member, and for a second end of said first cross-wise strap to extend beyond a medial side of said at least one resistance member a distance being one to three times said width of said at least one resistance member; and
wherein said second cross-wise strap comprises a length for a first end of said second cross-wise strap to extend beyond a lateral side of said at least one resistance member a distance being one to three times a width of said at least one resistance member, and for a second end of said second cross-wise strap to extend beyond a medial side of said at least one resistance member a distance being one to three times said width of said at least one resistance member.

5. The orthotic device according to claim 4, wherein each of said first cross-wise strap and said second cross-wise strap comprise a width being between one to three times a width of said at least one resistance member.

6. The orthotic device according to claim 5, wherein said at least one resistance member comprises a first resistance member and a second resistance member.

7. The orthotic device according to claim 6, wherein each said resistance member is fixedly secured using stitching.

8. The orthotic device of claim 7, wherein said elastic material each of said first tubular portion and said second tubular portion comprises a four-way stretch fabric.

9. The orthotic device according to claim 6, wherein a width of each of said first resistance member and said second resistance member comprises a width being 10 percent to 20 percent of a lateral extent of either said first tubular portion and said second tubular portion.

10. The orthotic device according to claim 6, wherein a width of each of said first resistance member and said second resistance member comprises a width being 20 percent to 35 percent of a lateral extent of either said first tubular portion and said second tubular portion.

11. The orthotic device according to claim 6, wherein a width of each of said first resistance member and said second resistance member comprises a width being 35 percent to 45 percent of a lateral extent of either said first tubular portion and said second tubular portion.

12. The orthotic device of claim 1, wherein each said resistance member comprises a two-way stretch fabric.

13. The orthotic device of claim 1, wherein each of said first cross-wise strap and said second cross-wise strap are formed of a non-stretch material.

14. An orthotic device comprising:
a first tubular portion, said first tubular portion formed of an elastic material;
a second tubular portion, said second tubular portion formed of an elastic material;
wherein said second tubular portion is joined to said first tubular portion to orient an axis of said second tubular portion at an angle to an axis of said first tubular portion, when undeformed;
wherein said first tubular portion is configured to encircle and elastically envelop a portion of a limb of the wearer on a first side of a joint;
wherein said second tubular portion is configured to encircle and elastically envelop a portion of the limb of the wearer on a second side of the joint;
a resistance member, said resistance member having a first end fixedly secured to a selective position on said first tubular portion, and a second end fixedly secured to a selective position on said second tubular portion;
wherein a length of said resistance member and a positioning of said first and second ends are configured to bias only up to fourteen degrees of the range of movement of the limb being just prior to full extension, to train the wearer's muscles and movement to be limited after said orthotic device is no longer being worn to prevent hyperextension;
a first cross-wise strap having a length that extends transversely around only a portion of said first tubular portion and is stitched to said first tubular portion, with a portion overlaying and being stitched to said first end of said resistance member, to distribute loads from said first end of said resistance member to said first tubular portion;
a second cross-wise strap having a length that extends transversely around only a portion of said second tubular portion and is stitched to said second tubular portion, with a portion overlaying and being stitched to said second end of said resistance member, to distribute loads from said second end of said resistance member to said second tubular portion.

15. The orthotic device according to claim 14, wherein said fixedly secured first end of said resistance member to said first tubular portion extends across a width of said first cross-wise strap; and
wherein said fixedly secured second end of said resistance member to said second tubular portion extends across a width of said second cross-wise strap.

16. The orthotic device according to claim 14, wherein said length of said first cross-wise strap is configured for a first end of said first cross-wise strap to extend beyond a lateral side of said resistance member a distance being one to three times a width of said resistance member, and for a second end of said first cross-wise strap to extend beyond a medial side of said resistance member a distance being one to three times said width of said resistance member; and wherein said length of said second cross-wise strap is configured for a first end of said second cross-wise strap to extend beyond a lateral side of said resistance member a distance being one to three times a width of said resistance member, and for a second end of said second cross-wise strap to extend beyond a medial side of said resistance member a distance being one to three times said width of said resistance member.

\* \* \* \* \*